US012350107B2

United States Patent
Prus et al.

(10) Patent No.: US 12,350,107 B2
(45) Date of Patent: Jul. 8, 2025

(54) SYSTEMS AND METHODS FOR PROVIDING TISSUE INFORMATION IN AN ANATOMIC TARGET REGION USING ACOUSTIC REFLECTORS

(71) Applicant: INSIGHTEC, LTD., Tirat Carmel (IL)

(72) Inventors: Oleg Prus, Haifa Ot (IL); Shahar Rinott, Haifa Ot (IL); Yoav Levy, Hinanit Ot (IL); Israel Schuster, Kiryat Tivon Ot (IL)

(73) Assignee: INSIGHTEC, LTD., Tirat Carmel (IL)

( * ) Notice: Subject to any disclaimer, the term of this patent is extended or adjusted under 35 U.S.C. 154(b) by 321 days.

(21) Appl. No.: 17/780,435

(22) PCT Filed: Dec. 18, 2020

(86) PCT No.: PCT/IB2020/001047
§ 371 (c)(1),
(2) Date: May 26, 2022

(87) PCT Pub. No.: WO2021/123905
PCT Pub. Date: Jun. 24, 2021

(65) Prior Publication Data
US 2023/0000469 A1 Jan. 5, 2023

Related U.S. Application Data

(60) Provisional application No. 62/949,597, filed on Dec. 18, 2019.

(51) Int. Cl.
*A61B 8/00* (2006.01)
*A61B 8/08* (2006.01)
(52) U.S. Cl.
CPC .......... *A61B 8/5223* (2013.01); *A61B 8/0891* (2013.01); *A61B 8/481* (2013.01)

(58) Field of Classification Search
CPC ..... A61B 8/5223; A61B 8/0891; A61B 8/481; A61B 8/5261; A61N 2007/0039;
(Continued)

(56) References Cited

U.S. PATENT DOCUMENTS 7,131,956 B1 * 11/2006 Pirazzoli ............. A61M 1/3441
604/4.01
2011/0077524 A1 3/2011 Oshiki
(Continued)

FOREIGN PATENT DOCUMENTS

CN 105073016 A 11/2015
CN 109689160 A 4/2019
(Continued)

OTHER PUBLICATIONS

JP 2003505209 B2 (Pirazzoli, English machine translation, Published (Year: 2003).*
(Continued)

*Primary Examiner* — Juan M Guillermety
(74) *Attorney, Agent, or Firm* — MORGAN, LEWIS & BOCKIUS LLP

(57) ABSTRACT

Various approaches for computationally characterizing tissue in an anatomic target region include generating multiple sonications to transient acoustic reflectors at or proximate to the target region; measuring reflection signals of the sonications off the transient acoustic reflectors; based on the measurements, identifying the reflection signals originating from single transient acoustic reflectors; and based at least in part on the identified reflection signals, generating a digital map including a tissue characteristic.

23 Claims, 9 Drawing Sheets

(58) Field of Classification Search
CPC .... A61N 2007/0052; A61N 2007/0078; A61N 2007/0095; A61N 7/00
See application file for complete search history.

(56) References Cited

U.S. PATENT DOCUMENTS

| | | |
|---|---|---|
| 2018/0035979 A1 | 2/2018 | Herbst |
| 2019/0175954 A1 | 6/2019 | Levy et al. |
| 2019/0192229 A1* | 6/2019 | Berlin .................. A61B 8/5246 |
| 2019/0350557 A1 | 11/2019 | Shi et al. |
| 2019/0365355 A1 | 12/2019 | Eldar et al. |
| 2021/0035296 A1* | 2/2021 | Mahrooghy ........... G06V 10/82 |

FOREIGN PATENT DOCUMENTS

| | | | | |
|---|---|---|---|---|
| WO | WO-2018020315 A1 * | 2/2018 | ........... | A61B 8/0808 |
| WO | 2019/175664 A1 | 9/2019 | | |
| WO | WO-2020128615 A1 * | 6/2020 | ............. | A61B 8/481 |

OTHER PUBLICATIONS

Insightec, Ltd., International Search Report and Written Opinion of the International Searching Authority mailed Apr. 12, 2021 for International Application No. PCT/IB2020/001047 (15 pages).

Insightec, Ltd., International Preliminary Report on Patentability of the International Searching Authority mailed Apr. 12, 2021 for International Application No. PCT/IB2020/001047 (15 pages).

Office Action issued in corresponding Japanese Application No. 2022-537015, dated Apr. 3, 2023, 5 pages.

First Chinese Office Action for related Chinese Patent Application No. 202080097062.2, dated Aug. 26, 2024, 7 pages.

\* cited by examiner

SYSTEMS AND METHODS FOR PROVIDING TISSUE INFORMATION IN AN ANATOMIC TARGET REGION USING ACOUSTIC REFLECTORS

RELATED APPLICATION

This application is a United States National Stage Application filed under 35 U.S.C. § 371 of PCT Patent Application Serial No. PCT/IB2020/001047, filed on Dec. 18, 2020, which claims the benefit of and priority to U.S. Provisional Patent Application No. 62/949,597, filed on Dec. 18, 2019, each of which is hereby incorporated by reference in its entirety.

FIELD OF THE INVENTION

The present invention relates, generally, to systems and methods for providing tissue information in an anatomic target region and, more particularly, to providing the tissue information using acoustic reflectors.

BACKGROUND

Tissue, such as a benign or malignant tumor or blood clot within a patient's skull or other body region, may be treated invasively by surgically removing the tissue or non-invasively by using, for example, thermal ablation. Both approaches may effectively treat certain localized conditions within the body, but involve delicate procedures to avoid destroying or damaging otherwise healthy tissue. Unless the healthy tissue can be spared or its destruction is unlikely to adversely affect physiological function, surgery may not be appropriate for conditions in which diseased tissue is integrated within healthy tissue.

Ultrasound therapy, as may be accomplished using focused ultrasound, has particular appeal for treating diseased tissue surrounded by or neighboring healthy tissue or organs because the effects of ultrasound energy can be confined to a well-defined target region. Ultrasonic energy may be focused to a zone having a cross-section of only a few millimeters due to relatively short wavelengths (e.g., as small as 1.5 millimeters (mm) in cross-section at one Mega-Hertz (1 MHz)). Moreover, because acoustic energy generally penetrates well through soft tissues, intervening anatomy often does not pose an obstacle to defining a desired focal zone. Thus, ultrasonic energy may be focused at a small target in order to ablate diseased tissue without significantly damaging surrounding healthy tissue.

In addition, ultrasound may be utilized to open the blood-brain barrier (BBB) in the treatment of neurological diseases. The BBB, formed by layers of cells in the central nervous system (CNS), prevents large molecules from entering the brain parenchyma, and thus presents one of the largest obstacles to treating many brain diseases. Specifically, the BBB prevents many therapeutic agents, such as drugs and gene-therapy vectors, from reaching a patient's brain tissue. For example, treatments for CNS infections, neurodegenerative diseases, congenital enzyme defects and brain cancer are all hampered by the ability of the BBB to block passage of, inter alia, antibiotics, anti-retroviral drugs, enzyme replacement therapy, gene preparations and anti-neoplastic drugs. It is thus desirable to using ultrasound energy to temporarily and locally "open" the BBB to permit therapeutic quantities of these agents to access the affected brain tissue.

An ultrasound focusing system generally utilizes an acoustic transducer surface, or an array of transducer surfaces, to generate an ultrasound beam. The transducer may be geometrically shaped and positioned to focus the ultrasonic energy at a "focal zone" corresponding to the target tissue mass within the patient. During wave propagation through the tissue, a portion of the ultrasound energy is absorbed, leading to increased temperature and, eventually, to cellular necrosis—preferably at the target tissue mass in the focal zone. The individual surfaces, or "elements," of the transducer array are typically individually controllable, i.e., their phases and/or amplitudes can be set independently of one another (e.g., using a "beamformer" with suitable delay or phase shift in the case of continuous waves and amplifier circuitry for the elements), allowing the beam to be steered in a desired direction and focused at a desired distance, and the focal zone properties to be shaped as needed. Thus, the focal zone can be rapidly displaced and/or reshaped by independently adjusting the amplitudes and/or phases of the electrical signal input into the transducer elements.

During a focused ultrasound procedure, system parameters are generally fixed for a given transducer array, but tissue homogeneity may vary significantly from patient to patient, and even between different tissue regions within the same patient and organ. Tissue inhomogeneity may decrease the intensity of the acoustic energy reaching the focal zone and may even move the location of the focal zone within the patient's body. In addition, different types of tissue may respond differently to the ultrasound application. For example, although exposing tissue to ultrasound may generally increase its permeability, different types of tissue may have different permeability responses. In addition, different types of tissue may have different degrees of viability in response to application of ultrasound.

Accordingly, to effectively and efficiently treat the target tissue while avoiding damage to non-target tissue, a need exists to acquire information about target and/or non-target tissue prior to and/or during the ultrasound procedure.

SUMMARY

The present invention relates to approaches for providing tissue information in an anatomic target region using reflections from one or more transient acoustic reflectors (e.g., one or more microbubbles) in proximity to (e.g., less than 5 mm away) one or more sonication locations that are themselves in proximity to or within the target region. In one embodiment, the transient acoustic reflectors are introduced into one or more blood vessels in proximity to the sonication location(s). An ultrasound transducer then transmits ultrasound waves to the reflector(s) and receives reflection signals therefrom. By analyzing the reflection signals, it is possible to obtain tissue information (e.g., tissue type, tissue condition, tissue anomaly, vascularity, tissue permeability and/or tissue viability) at the sonication locations and/or to map blood vessel(s) in the vicinity thereof. As used herein, the term "blood vessels" refers to venous and arterial passages and also to tissue adjacent thereto.

In some embodiments, the reflection signals are used to determine the tissue information only when the signals are sufficiently "consistent" (e.g., when the value of a consistency function of the travel times and/or phase delays associated therewith is maximized or exceeds a predetermined threshold). Additionally or alternatively, based on sufficiently consistent reflection signals, a characteristic (e.g., the concentration and/or flow rate) associated with the transient reflectors may be determined. For example, a larger amplitude of the reflection signal generally corresponds to a higher concentration and/or a higher flow rate of the reflectors. Further, based on the determined characteristic of the reflector, the presence and/or location of a lesion can be determined. For example, a slower flow rate at a portion of the blood vessel may indicate the presence of a nearby lesion.

In various embodiments, the tissue information provided by the sufficiently consistent reflection signals can be combined with information acquired using an imaging device (e.g., a computer tomography (CT) device or a magnetic resonance imaging (MRI) device) different from the ultrasound transducer via e.g., image registration. For example, the CT device may provide accurate locational information about the target region and the sufficiently consistent reflection signals may provide information such as the locations of the transient reflectors, a map of the blood vessels, tissue viability of the target/non-target regions, etc. This diverse information may advantageously be combined, thereby providing improved tissue characterization at the target/non-target regions for better diagnosis and/or therapy.

Further, the tissue information and/or the characteristic associated with the acoustic reflectors provided by the sufficiently consistent reflection signals may facilitate evaluation of the treatment effect of sonications at the target region during a therapeutic medical procedure. For example, as cancerous tissue in the target region is ablated, the concentration and/or the flow rate of the transient acoustic reflectors in blood vessels near the target may increase. Thus, by monitoring the concentration and/or the flow rate of the transient acoustic reflectors in local blood vessels, the treatment effect (e.g., ablation progress) and/or the viability of the target tissue during the therapeutic procedure can be effectively evaluated.

In some embodiments, multiple types (e.g., having different shell types, different contents, different half-lives in the body, different sizes, etc.) of the transient acoustic reflectors are utilized to obtain additional tissue information of the target and/or non-target. For example, relatively large microbubbles (e.g., having a diameter of a few micrometers) are introduced into the blood vessels prior to the relatively small microbubbles (e.g., having a diameter less than one micrometer or nanodroplets with diameters less than 100 nanometers). As a result, reflection signals from the relatively large microbubbles can provide information of the relatively large blood vessels and tissue associated therewith, and reflection signals from the relatively small microbubbles can provide additional information of the relatively small blood vessels and tissue associated therewith. In some embodiments, the transient acoustic reflectors include "targeted reflectors" that can be attached to specific types of receptors, biomolecules, cells or tissue. For example, the targeted reflectors can be microbubbles conjugated with antibodies. Due to affinity between the antibodies and their target proteins, the targeted reflectors may provide additional information about the cells or tissue in which the proteins are expressed. For example, microbubbles in the targeted reflectors may be attached to the membrane of epithelial cancer cells due to the affinity between the antibodies in the targeted reflectors and the cluster of differentiation 31 (CD31), which is expressed on the surface of all endothelial cancer cells. In addition, the targeted microbubbles may advantageously amplify the sonoporation effect on the cell membrane under relatively low peak negative acoustic pressure.

Accordingly, in one aspect, the invention pertains to a system for computationally characterizing tissue in an anatomic target region. In various embodiments, the system includes an ultrasound transducer having multiple transducer elements; and a controller configured to (a) cause the transducer to generate multiple sonications to transient acoustic reflectors at or proximate to the target region; (b) measure reflection signals of the sonications off the transient acoustic reflectors; (c) based on the measurements, identify the reflection signals originating from single transient acoustic reflectors; and (d) based at least in part on the identified reflection signals, generating a digital map of tissue within the target region, the map including a tissue characteristic (e.g., a tissue type, a tissue condition, a tissue anomaly, a degree of tissue viability, a degree of vascularity, and/or a degree of tissue permeability).

The system may further include means for introducing multiple transient acoustic reflectors to the tissue within the target region. The means for introducing the transient acoustic reflectors may include an administration device. In addition, the transient acoustic reflectors may include microbubbles. The microbubbles may have different characteristics (e.g., different shell types, different contents, different half-lives in a body and/or different sizes). Alternatively, the transient acoustic reflectors may include targeted reflectors. In one embodiment, the targeted reflectors include microbubbles conjugated with antibodies.

In various embodiments, the map further includes a mapping of blood vessels within the target region. In addition, the controller may be further configured to register the mapping of the blood vessels and/or the tissue characteristic with images acquired using an imaging device different from the ultrasound transducer. In some embodiments, the controller is further configured to determine concentrations of the transient acoustic reflectors in multiple portions of blood vessels based at least in part on the identified reflection signals and/or an injection rate of the transient acoustic reflectors. The controller may be further configured to determine an acoustic intensity distribution associated with one or more of the transient acoustic reflectors in one or more of the portions of the blood vessels based at least in part on the identified reflection signals; assign a weighting factor to each of the sub-regions within the blood vessel portion(s) based on the acoustic intensity associated therewith; and determine the concentration of the transient acoustic reflectors in the blood vessel portion(s) based at least in part on the weighted average of the acoustic intensities associated with the sub-regions. In addition, the controller is further configured to determine the tissue type, tissue condition, degree of tissue permeability, and/or degree of tissue viability associated with one or more portions of the target region based at least in part on the corresponding concentration of the transient acoustic reflectors.

In various embodiments, the controller is further configured to determine a flow rate of the transient acoustic reflectors in blood vessels based at least in part on the identified reflection signals. In addition, the controller may be further configured to map a location of a lesion within the target region based at least in part on the determined flow rate. In one implementation, the controller is further configured to cause the transducer to generate the second plurality of sonications to a sub-region within the target region so as to reduce a concentration of the transient acoustic reflectors therein; and determine the flow rate based at least in part on the identified reflection signals from the transient acoustic reflectors within the sub-region. Additionally, the controller may be further configured to determine the tissue information within the target region by computing a tissue aberration for one or more of the transducer elements using a physical model.

In another aspect, the invention relates to a method of computationally characterizing tissue in an anatomic target region. In various embodiments, the method includes (a) generating multiple sonications to transient acoustic reflectors at or proximate to the target region; (b) measuring reflection signals of the sonications off the transient acoustic reflectors; (c) based on the measurements, identifying the reflection signals originating from single transient acoustic reflectors; and (d) based at least in part on the identified reflection signals, generating a digital map of tissue within the target region, the digital map including a tissue characteristic (e.g., a tissue type, a tissue condition, a tissue anomaly, a degree of tissue viability, a degree of vascularity, and/or a degree of tissue permeability).

The method may further include introducing multiple transient acoustic reflectors to the tissue within the target region. The transient acoustic reflectors may include microbubbles. The microbubbles may have different characteristics (e.g., different shell types, different contents, different half-lives in a body and/or different sizes). Alternatively, the transient acoustic reflectors may include targeted reflectors. In one embodiment, the targeted reflectors include microbubbles conjugated with antibodies.

In various embodiments, the digital map further includes a mapping of blood vessels within the target region. In addition, the method may further include registering the mapping of the blood vessels and/or the tissue characteristic with images acquired using an imaging device different from an ultrasound transducer. In some embodiments, the method further includes determining concentrations of the transient acoustic reflectors in multiple portions of blood vessels based at least in part on the identified reflection signals and/or an injection rate of the transient acoustic reflectors.

The method may further include determining an acoustic intensity distribution associated with one or more of the transient acoustic reflectors in one or more of the portions of the blood vessels based at least in part on the identified reflection signals; assigning a weighting factor to each of the sub-regions within the blood vessel portion(s) based on the acoustic intensity associated therewith; and determining the concentration of the transient acoustic reflectors in the blood vessel portion(s) based at least in part on the weighted average of the acoustic intensities associated with the sub-regions. In addition, the method may further include determining the tissue type, tissue condition, degree of tissue permeability, and/or degree of tissue viability associated with one or more portions of the target region based at least in part on the corresponding concentration of the transient acoustic reflectors.

In various embodiments, the method further includes determining a flow rate of the transient acoustic reflectors in blood vessels based at least in part on the identified reflection signals. In addition, the method may further include mapping a location of a lesion within the target region based at least in part on the determined flow rate. In one implementation, the method further includes generating the second plurality of sonications to a sub-region within the target region so as to reduce a concentration of the transient acoustic reflectors therein; and determining the flow rate based at least in part on the identified reflection signals from the transient acoustic reflectors within the sub-region. Additionally, the method may further include determining the tissue information within the target region by computing a tissue aberration for one or more transducer elements using a physical model.

Another aspect of the invention relates to a system for computationally revising a digital acoustic image of an anatomic target region. In various embodiments, the system includes an ultrasound transducer; and a controller configured to cause the transducer to generate one or more sonications focused on tissue in the anatomic target region; measure reflection signals of the sonication(s) off the tissue; compute a tissue aberration; and reconstruct the digital acoustic image based at least in part on the measured reflection signals and the computed tissue aberration to thereby produce the revised digital acoustic image.

The acoustic image may represent an acoustic field generated by the sonication(s) focused on the tissue in the anatomic target region. Additionally or alternatively, the acoustic image may represent an acoustic field generated by the sonication(s) at a location of one or more acoustic reflectors. In some embodiments, the acoustic image represents an acoustic field generated by the sonication(s) focused on the tissue in the anatomic target region and at a location of the acoustic reflector(s). Additionally, the controller may be further configured to compute the tissue aberration using a physical model. In one implementation, the system further includes an administration device for introducing the acoustic reflector(s).

In yet another aspect, the invention pertains to a method of computationally revising a digital acoustic image of an anatomic target region. In various embodiments, the method includes generating one or more sonications focused on tissue in the anatomic target region; measuring reflection signals of the sonication(s) off the tissue; computing a tissue aberration; and reconstructing the digital acoustic image based at least in part on the measured reflection signals and the computed tissue aberration to thereby produce the revised digital acoustic image.

The acoustic image may represent an acoustic field generated by the sonication(s) focused on the tissue in the anatomic target region. Additionally or alternatively, the acoustic image may represent an acoustic field generated by the sonication(s) at a location of one or more acoustic reflectors. In some embodiments, the acoustic image represents an acoustic field generated by the sonication(s) focused on the tissue in the anatomic target region and at a location of the acoustic reflector(s). Additionally, the method may further include computing the tissue aberration using a physical model.

Still another aspect of the invention relates to a system for evaluating a treatment effect (e.g., a tissue aberration and/or a temperature increase) on a target region. In various embodiments, the system includes an ultrasound transducer; and a controller configured to (a) cause the transducer to generate multiple sonications to transient acoustic reflectors at or proximate to the target region in accordance with a sonication plan; (b) measure reflection signals of the sonications off at least some of the transient acoustic reflectors; and (c) based at least in part on the measured reflection signals, determine the treatment effect of the sonications on the target region. The sonication plan may be a treatment plan or a diagnosis plan. In one implementation, the system further includes an administration device for introducing the transient acoustic reflectors at or proximate to the target region.

In various embodiments, the controller is further configured to determine a concentration and/or a flow rate of the transient acoustic reflectors in the blood vessel based at least in part on the measured reflection signals; and determine the treatment effect based at least in part on the determined concentration and/or flow rate. In addition, the controller may be further configured to determine, based at least in part on an injection rate of the transient acoustic reflectors, the concentrations of the transient acoustic reflectors in multiple portions of blood vessels located in proximity to the target region. The controller may be further configured to determine an acoustic intensity distribution associated with one or more of the transient acoustic reflectors in one or more of the portions of the blood vessels based at least in part on the measured reflection signals; assign a weighting factor to each of the sub-regions within the blood vessel portion(s) based on the acoustic intensity associated therewith; and determine the concentration of the transient acoustic reflectors in the blood vessel portion(s) based at least in part on the weighted average of the acoustic intensities associated with the sub-regions. Additionally, the controller may be further configured to cause the transducer to generate the second sonications to a sub-region within the target region so as to reduce a concentration of the transient acoustic reflectors therein; and determine the flow rate based at least in part on the measured reflection signals from the transient acoustic reflectors within the sub-region.

In another aspect, the invention relates to a method of evaluating a treatment effect (e.g., a tissue aberration and/or a temperature increase) on a target region. In various embodiments, the method includes (a) generating multiple sonications to transient acoustic reflectors at or proximate to the target region in accordance with a sonication plan; (b) measuring reflection signals of the sonications off at least some of the transient acoustic reflectors; (c) based at least in part on the measured reflection signals, determining the treatment effect of the sonications on the target region. The sonication plan may be a treatment plan or a diagnosis plan. In one implementation, the method further includes causing the transducer to generate the second sonications to a sub-region within the target region so as to reduce a concentration of the transient acoustic reflectors therein; and determining the flow rate based at least in part on the measured reflection signals from the transient acoustic reflectors within the sub-region.

The method may further include determining a concentration and/or a flow rate of the transient acoustic reflectors in the blood vessel based at least in part on the measured reflection signals; and determining the treatment effect based at least in part on the determined concentration and/or flow rate. In addition, the method may further include determining, based at least in part on an injection rate of the transient acoustic reflectors, the concentrations of the transient acoustic reflectors in multiple portions of blood vessels located in proximity to the target region. In some embodiments, the method further includes determining an acoustic intensity distribution associated with one or more of the transient acoustic reflectors in one or more of the portions of the blood vessels based at least in part on the measured reflection signals; assigning a weighting factor to each of the sub-regions within the blood vessel portion(s) based on the acoustic intensity associated therewith; and determining the concentration of the transient acoustic reflectors in the blood vessel portion(s) based at least in part on the weighted average of the acoustic intensities associated with the sub-regions.

As used herein, the term "substantially" means±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
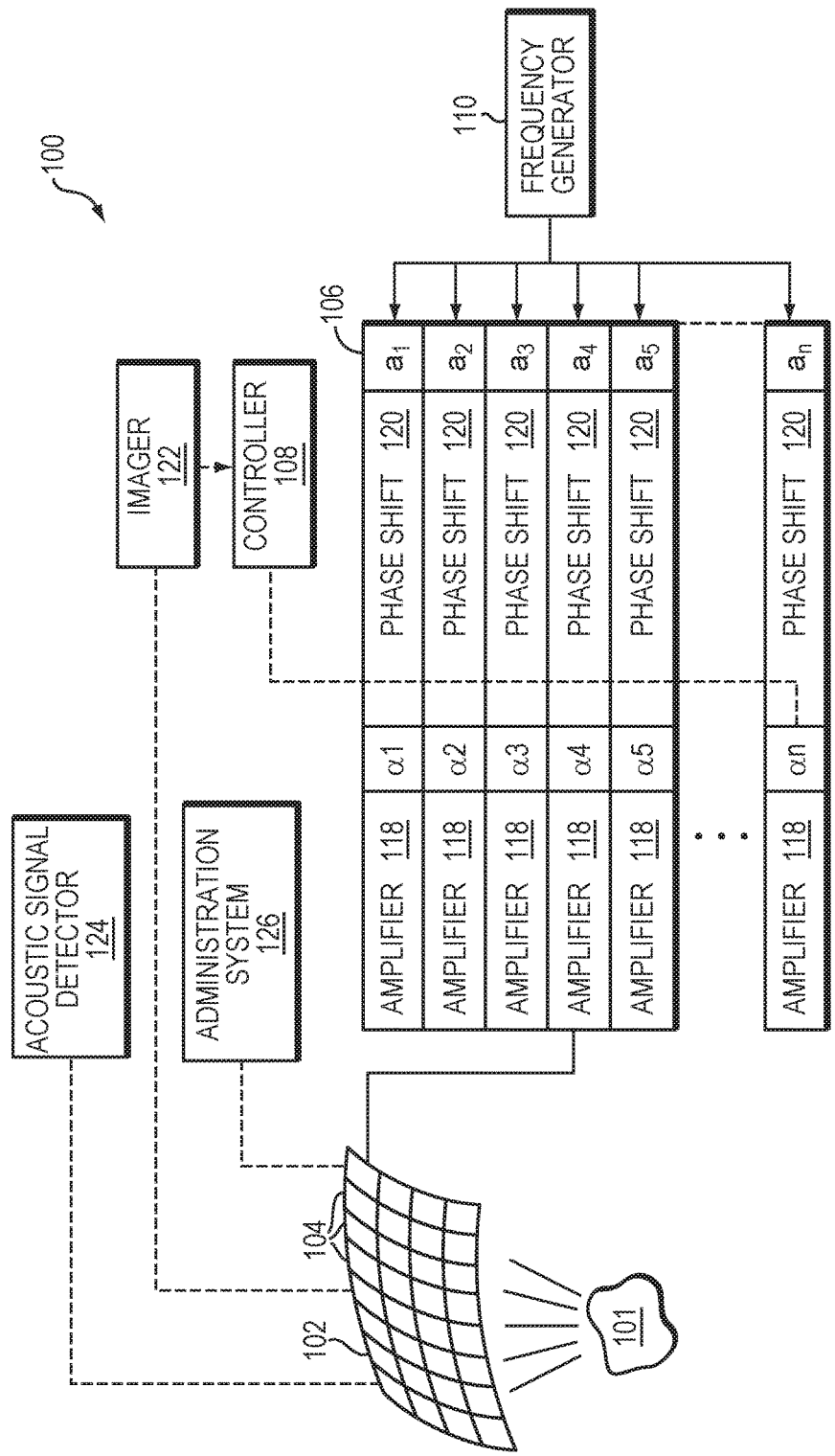
FIG. 1 schematically depicts an exemplary ultrasound system in accordance with various embodiments.

FIG. 1 illustrates an exemplary ultrasound system 100 for providing tissue information of an anatomic target region 101. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placement on the surface of the skull or a body part other than the skull, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase delay circuit 120; each drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through inhomogeneous tissue (e.g., the patient's skull) onto the target region (e.g., a region in the patient's brain). Via adjustments of the amplification factors and/or the phase shifts, a desired shape and intensity of a focal zone may be created at the target region.

The amplification factors and phase shifts may be computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, to determine the frequency, phase shifts and/or amplification factors of the transducer elements 104. In certain embodiments, the controller computation is based on information about the characteristics (e.g., structure, thickness, density, etc.) of the skull and their effects on propagation of acoustic energy. In various embodiments, such information is obtained from an imager 122, such as an MRI device, a CT device, a positron emission tomography (PET) device, a single-photon emission computed tomography (SPECT) device, or an ultrasonography device. The imager 122 may provide a set of two-dimensional images suitable for reconstructing a three-dimensional image of the skull from which thicknesses and densities can be inferred; alternatively, image acquisition may be three-dimensional. In addition, image-manipulation functionality may be implemented in the imager 122, in the controller 108, or in a separate device.

The system 100 may be modified in various ways within the scope of the invention. For example, the system may further include an acoustic-signal detector (e.g., a hydrophone) 124 that measures transmitted or reflected ultrasound, and which may provide the signals it receives to the controller 108 for further processing. The reflection and transmission signals may also provide an alternative or additional source for determining the phase shifts and/or amplification factors or feedback for the phase and amplitude adjustments of the beamformer 106 as further described below. The system 100 may contain a positioner for arranging the array 102 of transducer elements 104 with respect to the patient's skull. In order to apply ultrasound therapy to body parts other than the brain, the transducer array 102 may take a different (e.g., cylindrical) shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Figure 2A:
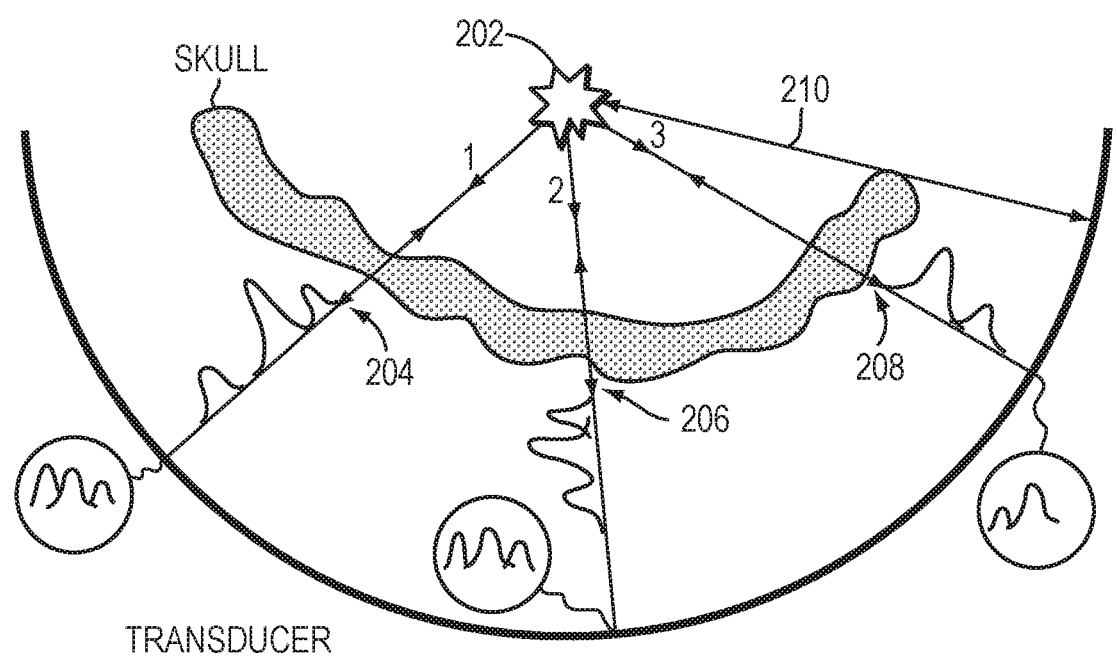
FIG. 2A depicts one or more transient acoustic reflectors located in proximity to one or more target regions in accordance with various embodiments.

With reference to FIG. 2A, in order to acquire tissue information of the target region 101 and/or the non-target region in proximity to the target region, in various embodiments, one or more transient acoustic reflectors (e.g., microbubbles) 202 are introduced into or proximate to the target region 101. The microbubbles 202 may be generated by applying acoustic energy from the transducer elements 104 to the target 101. The microbubbles 202 can be formed due to the negative pressure produced by the propagating ultrasonic waves or when the heated liquid ruptures and is filled with gas/vapor. Because of their encapsulation of gas, the microbubble(s) 202 may act as reflectors of the ultrasound waves and transmit coherent omnidirectional signals 204-208 to the transducer 102; the reflection signals 204-208 can be substantially concurrently detected by the transducer elements 104 and/or acoustic signal detector 124 associated therewith. Based on analysis of the reflection signals, the controller 108 may obtain information of the tissue information at the target region 101 as further described below. Approaches to generating microbubbles utilizing ultrasound waves are provided, for example, in U.S. Patent Publication No. 2019/0308038, the entire content of which is incorporated herein by reference.

Additionally or alternatively, the acoustic reflector 202 may be introduced into the patient's body intravenously; the transient reflector may either be injected systemically into the patient or locally into the target region 101 using an administration system 126. For example, the transient reflector 202 may include or consist of one or more microbubbles introduced into the patient's brain in the form of liquid droplets that subsequently vaporize to form the microbubbles; or as gas-filled bubbles entrained within a liquid carrier, e.g., a conventional ultrasound contrast agent. Alternatively, other substances suitable for cavitation nucleation can be administered instead of bubbles (see, e.g., https://www.springer.com/cda/content/document/cda downloaddocument/9783642153426-cl.pdf?SGWID=0-0-45-998046-p174031757).

In some embodiments, after the transient reflector 202 is generated and/or introduced into the target region 101, the controller 108 may activate at least some of the transducer elements 104 to transmit a series of sonications to the microbubbles located at the target region 101. In one implementation, the transducer elements 104 possess both transmit and detect capabilities. Thus, at least some of the transducer elements 104 may be operated to measure acoustic signals reflected from the target region 101 as described, for example, in International Application No. PCT/IB2019/000644 (filed on Jun. 4, 2019), the contents of which are incorporated herein by reference. Additionally or alternatively, ultrasound reflections from the transient reflector 202 at the target region 101 may be measured using the acoustic-signal detector 124.

Figure 2B:
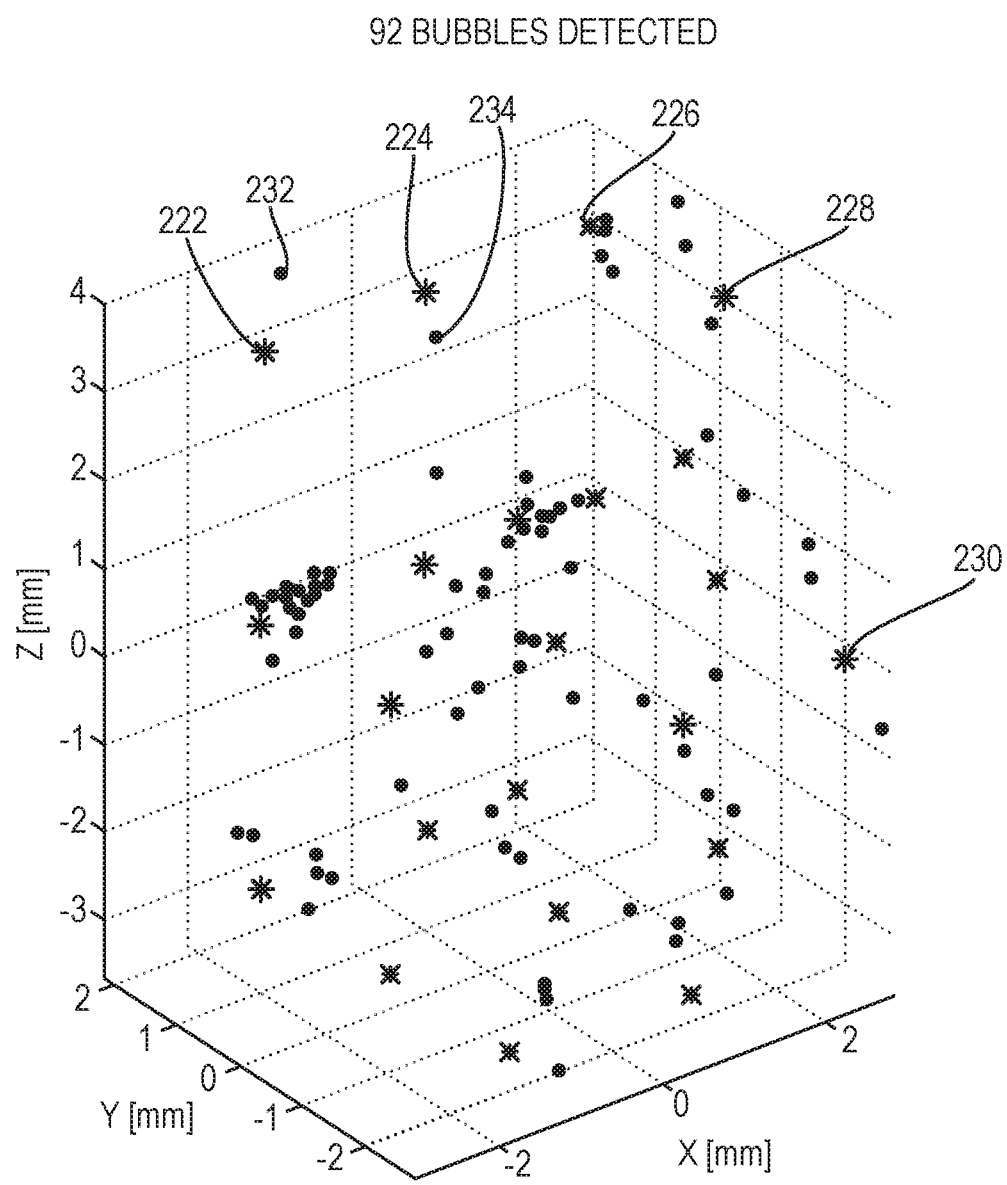
FIG. 2B depicts application of sonications to multiple locations in proximity to a target region in accordance with various embodiments.

The measured reflection signals may then be fed to the controller 108 for analysis; based thereon, the controller 108 may determine information of the tissue located in proximity to and/or within the target region and/or a characteristic associated with the transient acoustic reflector as further described below. In various circumstances, the reflection signals from the transient reflector 202 have relatively low quality (e.g., the signal-to-noise ratios (SNRs) are below a threshold); analysis based thereon may therefore result in inaccurate determination of the tissue information at the target. FIG. 2B illustrates an approach to solving this problem. The ultrasound transducer 102 may be activated to sequentially generate multiple foci at various sonication locations 222-230 that are in proximity to the target region 101 (e.g., less than 5 mm away) or within the target region 101, and each location may have one or more transient reflectors 202 associated therewith. For example, the transducer elements 104 may generate one or more series of sonications to the first sonication location 222 and measure the reflections from the transient reflector 232 located in proximity thereto. Subsequently, the transducer elements 104 may generate another one or more series of sonications to the second sonication location 224 and measure the reflections from the transient reflector 234 associated therewith. This process may continue until a desired number (e.g. at least 10) of the reflection signals from the sonication locations in proximity to the target 101 are measured.

In various embodiments, the sonication locations 222-230 are determined based on the image(s) acquired by the imager 122 and/or the ultrasound transducer 102. For example, the imager 122 may acquire images of the target and/or non-target regions; and the ultrasound transducer 102 may acquire images of the transient reflector(s) 202 in the target/non-target regions based on the reflection signals therefrom as further described below. Based on the acquired images of the target/non-target regions and the transient reflectors associated therewith, the controller 108 may select the sonication locations 222-230 that are near (e.g., less than 5 mm away) and/or at the target region and having one or more transient reflectors in proximity to thereto (e.g., less than 5 mm away).

In some embodiments, upon collection of the reflection signals from all (or at least some) of the sonication locations, an initial signal-processing procedure is performed to select signals that are more likely to be from the transient reflectors. This approach may advantageously eliminate (or at least reduce) usage of reflections from the background reflectors (e.g., the skull), which are less relevant (or irrelevant) to characterizing the target region. As used herein, the term "transient reflector" refers to an acoustic reflector that dissipates or evolves with time during sonications (e.g., microbubbles) and the term "background reflector" refers to an acoustic reflector that does not dissipate or evolve significantly during sonication (e.g., the skull). In addition, a signal-selection approach may be implemented to select the reflection signals that are from single reflectors. In one embodiment, the signal-selection approach selects the reflection signals based on consistency therebetween. For example, the reflection signals are considered to have sufficient consistency when the value of a consistency function of the phase delays (or travel times) associated with the reflection signals is maximized or exceeds a predetermined threshold (e.g., 40%). By using the reflection signals having sufficient consistency, artifacts exhibited in the signals due to low SNRs and/or vibrations from the multiple microbubbles may advantageously be eliminated (or at least reduced); this thereby provides more accurate information about the tissue located in proximity to or within the target region and/or a characteristic associated with the transient reflectors. In addition, the computational complexity of analyzing the reflection signals can be significantly reduced. Further details concerning the initial signal-processing procedure and signal-selection approach are provided, for example, in PCT Publication No. WO 2020/128615, the entire contents of which are incorporated herein by reference.

Figure 3:
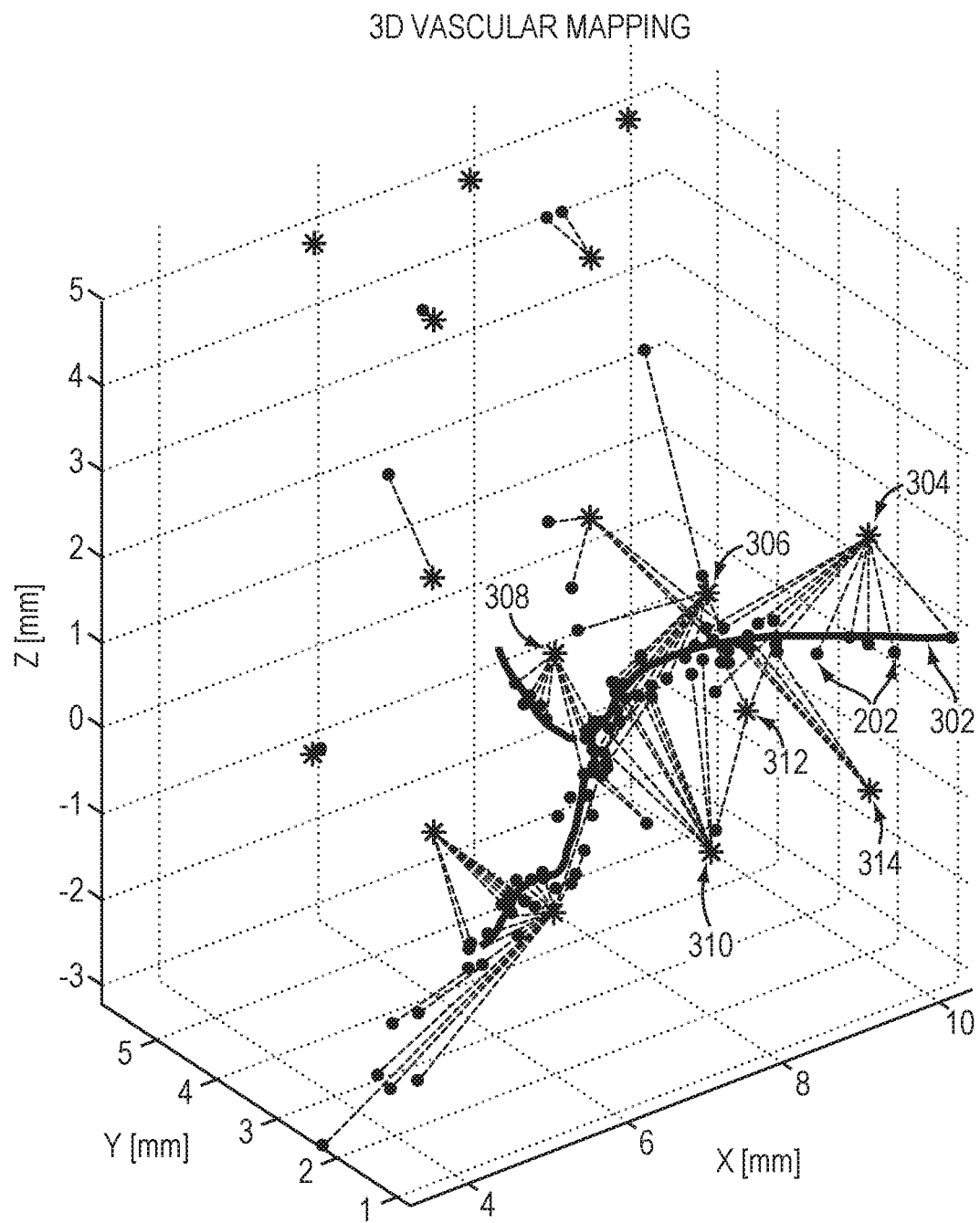
FIG. 3 schematically depicts transient acoustic reflectors in one or more blood vessels in proximity to one or more sonication locations in accordance with various embodiments.

In various embodiments, based on the selected reflection signals that have sufficient consistency, the controller 108 can generate one or more images of the transient reflectors and/or determine a characteristic (e.g., a concentration or a flow rate) associated with the transient reflectors 202. For example, referring to FIG. 3A, transient acoustic reflectors 202 may be introduced (e.g., by the administration device 126) with a predetermined injection rate (e.g., 1 cc/min) into one or more blood vessels 302 in proximity to the identified sonication locations 304-314; based on the injection rate and the reflection signals from the reflectors 202 received from each portion of the blood vessel 302, the controller 108 may determine the concentration of the transient acoustic reflectors in the corresponding portion of the blood vessel 302. Generally, the higher the injection rate and/or the larger the amplitude of the selected reflection signal, the higher the reflector concentration will be. In various embodiments, a relationship between injection rates and reflector concentrations and/or a relationship between the amplitudes of the sufficiently consistent reflection signals and reflector concentrations can be established prior to performing measurements of the reflection signals. These relationships may be empirically obtained from a pre-clinical study, a pre-treatment procedure, and/or from known literature. Alternatively, the relationship may be computationally determined using a physical model. For example, using conventional techniques implemented without undue experimentation, the physical model may predict the amplitudes associated with the sufficiently consistent reflection signals based on information about the geometry of the transducer elements 104 and their locations and orientations relative to the sonication locations 304-314, the power levels and phases of ultrasound waves transmitted from the elements 104, material properties (e.g., the energy absorption of the tissue or the speed of sound at the employed frequency) of the target tissue and intervening tissue along the beam path, as well as the injection rate and/or concentrations of the reflectors in different portions of the blood vessel 302. The material properties may be collected using the imager 122 as described above and/or other suitable devices. For example, based on the acquired images, a tissue model characterizing one or more material characteristics of the intervening tissue and the target tissue may be established. The tissue model may take the form of a 3D arrangement of cells corresponding to voxels representing the intervening and/or target tissue; the cells have attributes whose values represent characteristics of the tissue, such as the absorption coefficient, that are relevant to the energy absorption. The voxels are obtained tomographically by the imager 122 and the type of tissue that each voxel represents can be determined automatically by conventional tissue-analysis software. Using the determined tissue types and a lookup table of tissue parameters (e.g., absorption coefficient by type of tissue), the cells of the tissue model may be populated. Further detail regarding creation of a tissue model that identifies the energy absorption coefficient, heat sensitivity and/or thermal energy tolerance of various tissues may be found in U.S. Patent Publication No. 2012/0029396, the entire disclosure of which is hereby incorporated by reference.

Figure 4A:
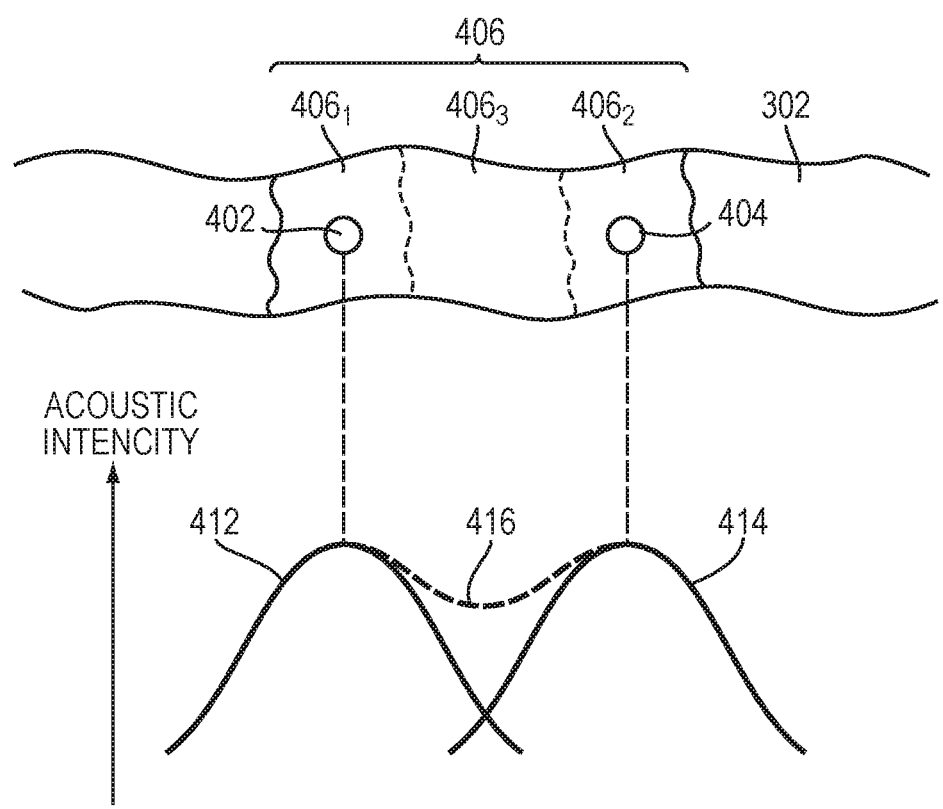
FIG. 4A schematically depicts two acoustic focus points located in two sub-regions within a blood vessel and their corresponding acoustic intensity distributions in accordance with various embodiments.

Additionally or alternatively, the controller 108 may analyze the sufficiently consistent reflection signals to determine the acoustic intensity distributions associated with the transient acoustic reflectors in each portion of the blood vessel 302. FIG. 4A depicts two acoustic focus points 402, 404 located in two sub-regions $406_1$, $406_2$ within a portion 406 of the blood vessel 302 and their corresponding acoustic intensity distributions 412, 414. The controller 108 operates the transducers to generate an acoustic field with desired properties at the focus, using, for example, a grid of sonications exemplified by points 402, 404.

Figure 4B:
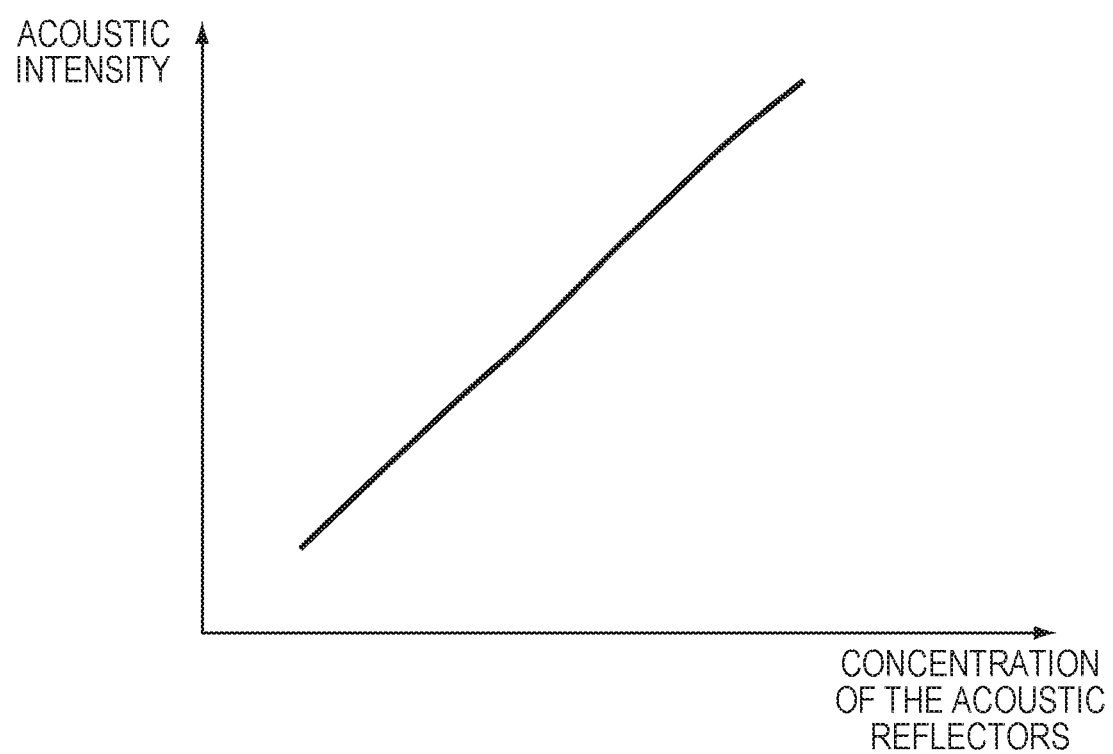
FIG. 4B illustrates a relationship between acoustic intensities and concentrations of the transient acoustic reflectors in accordance with various embodiments.

Typically, the acoustic intensity has a peak value at the location of the focus; the acoustic intensity gradually decreases as the distance from the focus increases. If the acoustic intensity in the region $406_3$ exceeds a physical threshold (e.g., 1 MP), there may be acoustic reflectors that are detected by measurements, but with lower probability. Thus, in some embodiments, the controller 108 assigns a weighting factor to each sub-region within a portion of the blood vessel based on the acoustic intensity associated therewith. For example, the sub-region $406_3$ corresponding to the overlap location 416 has a cumulative acoustic intensity lower than that of the focus points 402, 404; hence, this location receives a larger weighting factor, while the sub-regions $406_1$, $406_2$ corresponding to the locations of the focus points 402, 404 may be assigned smaller weighting factors. Thereafter, the controller 108 may determine the concentration of the transient acoustic reflectors in the portion 406 of the blood vessel 302 based on a weighted average of the acoustic intensities associated with the sub-regions $406_{1-3}$ and a relationship between the acoustic intensities and reflector concentrations (as depicted in FIG. 4B). Again, this relationship may be empirically obtained from a pre-clinical study, a pre-treatment procedure, and/or from known literature and/or computationally determined using the physical model as described above.

In some embodiments, the controller 108 can determine the flow rate of the transient reflectors in various portions of the blood vessel 302 using the sufficiently consistent reflection signals. Again, typically, the larger the number of consistent signals and/or the larger the amplitudes of the reflection signals, the higher will be the flow rate of the reflectors; and the relationship between the number of consistent signals and/or the amplitudes of the reflection signals and the flow rates of the reflectors can be established empirically and/or using the physical model as described above prior to performing measurements of the reflection signals.

In various embodiments, the transient acoustic reflectors in an identified portion of the blood vessel 302 are depleted or at least reduced by activating the transducer 102 to transmit sonications thereto. Thereafter, based on measurements of the sufficiently consistent reflection signals from the transient acoustic reflectors within the identified sub-region, the controller 108 may determine the flow rate therein. Again, larger number of consistent signals and/or the larger the reflection-signal amplitudes and/or shorter periods of detecting the reflection signals after depletion (or reduction) of the acoustic reflectors correspond to the larger flow rate, and this relationship can be established empirically or using the physical model prior to the measurements of the reflection signals.

In some embodiments, the controller 108 further determines information regarding the tissue located in proximity to the blood vessel 302. For example, a slower flow rate at a portion of the blood vessel may indicate the presence of a lesion. Thus, by comparing the flow rate along the blood vessel, the presence and/or the location of a lesion can be identified. In addition, because the anatomical and/or material properties of the tissue in proximity to the blood vessel may affect the concentration and/or the flow rate of the transient acoustic reflectors, the controller 108, upon determining the concentration/flow rate of the reflectors in a portion of the blood vessel, may generate a digital map to provide tissue information (e.g., tissue type, tissue condition, tissue permeability, tissue anomaly, vascularity, and/or tissue viability) in the corresponding region in proximity to the portion of the blood vessel. In one embodiment, the sufficiently consistent reflection signals are selected such that they are from a specific location (e.g., the portion of the blood vessel that is in proximity to one of the sonication locations). As a result, the tissue characteristics (e.g., the type, condition, anomaly, vascularity, permeability and/or viability) associated with the sonication location can be determined. Further details regarding selection of the reflection signals based on the locations of the reflectors are provided, for example, in U.S. Patent Publication No. 2018/0206816, the entire contents of which are incorporated herein by reference.

In various embodiments, based on analysis of the sufficiently consistent reflection signals, the controller 108 may generate an image of the reflectors and/or mapping of the blood vessel 302 in which the transient reflectors 202 are located. In addition, the controller 108 may register the generated mapping of the blood vessels (and/or the characteristic of the tissue in proximity to or within the target region) with images that are acquired using an imaging device (e.g., a CT device or an MRI device) different from the ultrasound transducer. This may advantageously allow different types of information provided by different imaging devices to be combined, thereby providing useful details about the tissue information at the target/non-target regions for better diagnosis. For example, the CT device may provide accurate locational information about the target region and the sufficiently consistent reflection signals may provide information such as the locations of the transient reflectors, the mapping of the blood vessels, the tissue viability of the target/non-target regions, etc. Approaches to registering information (e.g., images) acquired using two or more imaging systems as described, for example, in U.S. Pat. No. 9,934,570, the entire contents of which are incorporated herein by reference.

Further, because ultrasound energy can be employed therapeutically—e.g., to heat and ablate diseased (e.g., cancerous) tissue without causing significant damage to surrounding healthy tissue—the tissue information and/or the characteristic of the acoustic reflectors provided by the sufficiently consistent reflection signals may allow the treatment effect of the sonications on the target region to be evaluated during a therapeutic medical procedure. In various embodiments, to ablate the target tissue, the ultrasound waves from the transducer elements 104 are focused at the target region 101 using an autofocusing approach that involves the use of one or more transient reflectors. As described above, the transient reflectors may be generated and/or introduced in proximity to (e.g., less than 5 mm away) one or more sonication locations that are in proximity to or at the target region. Upon introduction or generation of the transient reflector near the target 101, the transducer 102 is activated to apply a series of sonications thereto; reflection signals from the reflector 202 may be detected by the transducer 102 and/or the acoustic-signal detection device 124 associated with the transducer elements. Optionally, the measured signals may be selected using the initial signal-processing approach and/or signal-selection approach described above.

Subsequently, the selected signals can be provided to the controller 108 to obtain information, such as the amplitudes and/or phases, associated with the reflections; these may be compared to the amplitudes and/or phases associated with the transmitted ultrasound waves from the transducer elements 104. Based on the deviations therebetween, configurations (e.g., amplitudes and/or phases) of one or more transducer elements 104 may be adjusted so as to compensate for the deviations, thereby improving the focusing properties. In some embodiments, this autofocusing procedure is iteratively performed until optimal focusing properties are achieved. Approaches for autofocusing an ultrasound beam at the target region are provided, for example, in PCT Publication No. WO 2018/020315 and U.S. Patent Application No. 62/781,258 (filed on Dec. 18, 2018); the entire contents of these applications are incorporated herein by reference.

In various embodiments, the controller 108 operates the transducer elements based on the configurations determined using the autofocusing approach so as to treat the target tissue (e.g., cancerous tissue). As the target cancerous tissue is ablated, the concentration and/or the flow rate of the transient acoustic reflectors in the blood vessel in proximity to the target may increase. Thus, in one embodiment, the controller 108 can analyze the sufficiently consistent reflection signals from the acoustic reflectors to monitor the concentration and/or the flow rate of the transient acoustic reflectors in the blood vessel, and based thereon, determine the treatment effect (e.g., the tissue ablation progress) and/or the viability of the target tissue.

In some embodiments, the controller 108 computationally reconstructs an acoustic field in the target tissue and/or the location(s) of the acoustic reflector(s) based on the reflection signals therefrom. For example, upon applying sonications to the target tissue and/or the transient acoustic reflector(s) in proximity thereto, at least some of the transducer elements 104 may simultaneously record reflection signals from the acoustic reflector(s); based thereon, the sources of the emissions can be estimated through back-propagation to different image coordinates so as to reconstruct two- or three-dimensional acoustic images (e.g., acoustic-field maps) of the activity. The image amplitude reflects the intensity of the acoustic emissions integrated across the array elements 104.

Additionally or alternatively, the controller 108 may computationally reconstruct the acoustic image of the target/non-target region based on the tissue information (e.g., tissue aberration and/or temperature increase) associated therewith. For example, the controller may implement the physical model described above to compute tissue aberration and/or temperature increase at the target and/or non-target region. Information of the computed tissue aberrations and/or temperature increases may then be combined with information acquired from the reflection signals off the target/non-target region to reconstruct the acoustic image at the target and/or non-target region.

Figure 5A:
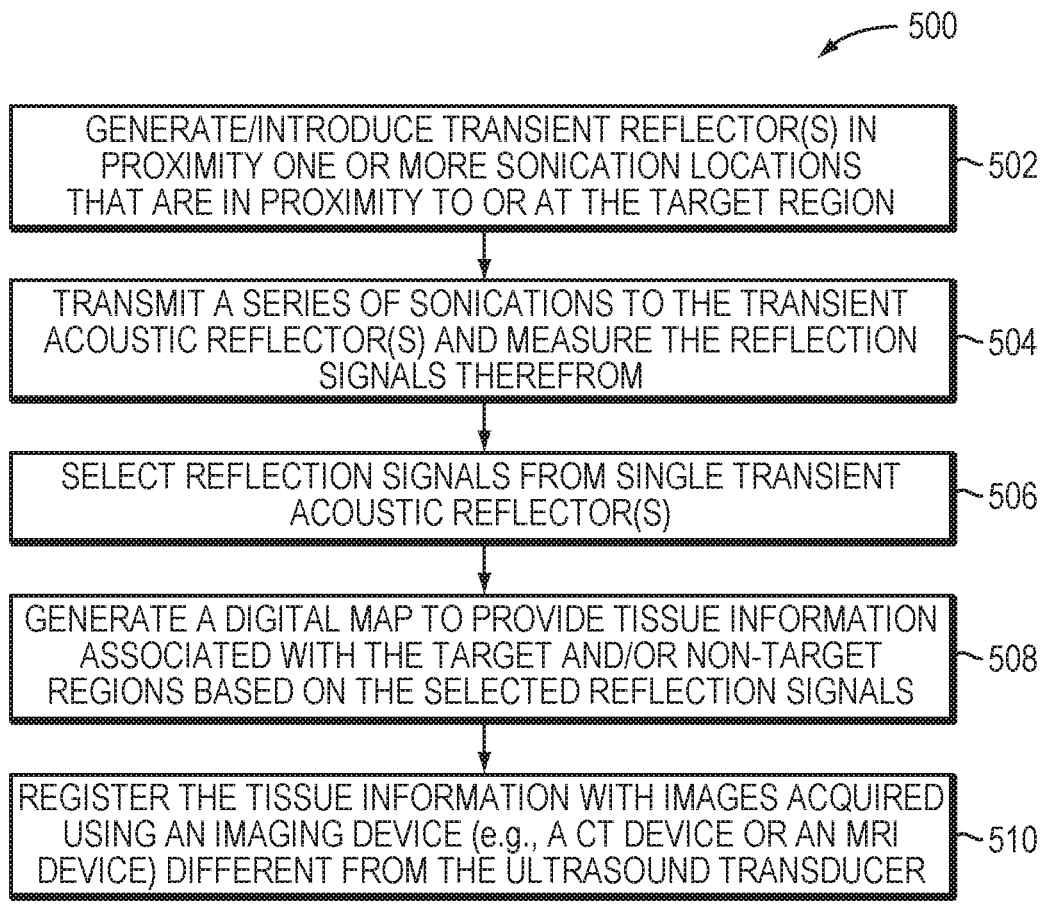
FIG. 5A is a flow chart illustrating an approach for acquiring information about target and/or non-target tissue and generating a digital map providing the tissue information prior to and/or during an ultrasound procedure in accordance with various embodiments.

FIG. 5A illustrates an exemplary approach 500 for acquiring information about target and/or non-target tissue and generating a digital map providing the tissue information prior to and/or during the ultrasound procedure in accordance herewith. In a first step 502, the transient acoustic reflectors (e.g., microbubbles) having an initial concentration are generated and/or introduced with an injection rate in proximity to (e.g., less than 5 mm away) one or more sonication locations that are in proximity to or at the target region. In a second step 504, at least some of the transducer elements 104 are activated to transmit a series of sonications to the transient reflector(s); reflection signals from the transient reflector(s) are measured using, for example, the acoustic-signal detector 124 and/or the transducer elements 104. In a third step 506, the controller 108 may implement an initial signal-processing approach and/or a signal-selection approach to select reflection signals from single transient acoustic reflector(s) (as opposed to the background reflector(s)). Based on the selected reflection signals, the controller 108 may generate a digital map to provide tissue information associated with the target and/or non-target regions (step 508). The tissue information may include, for example, a mapping of blood vessels and/or a characteristic (e.g., a tissue type, tissue condition, tissue permeability, tissue viability, tissue anomaly, vascularity, tissue aberration, tissue temperature) of the tissue. In various embodiments, the controller registers the tissue information with images acquired using an imaging device (e.g., a CT device or an MRI device) different from the ultrasound transducer to provide more details about the tissue information in the target/non-target regions (step 510).

Figure 5B:
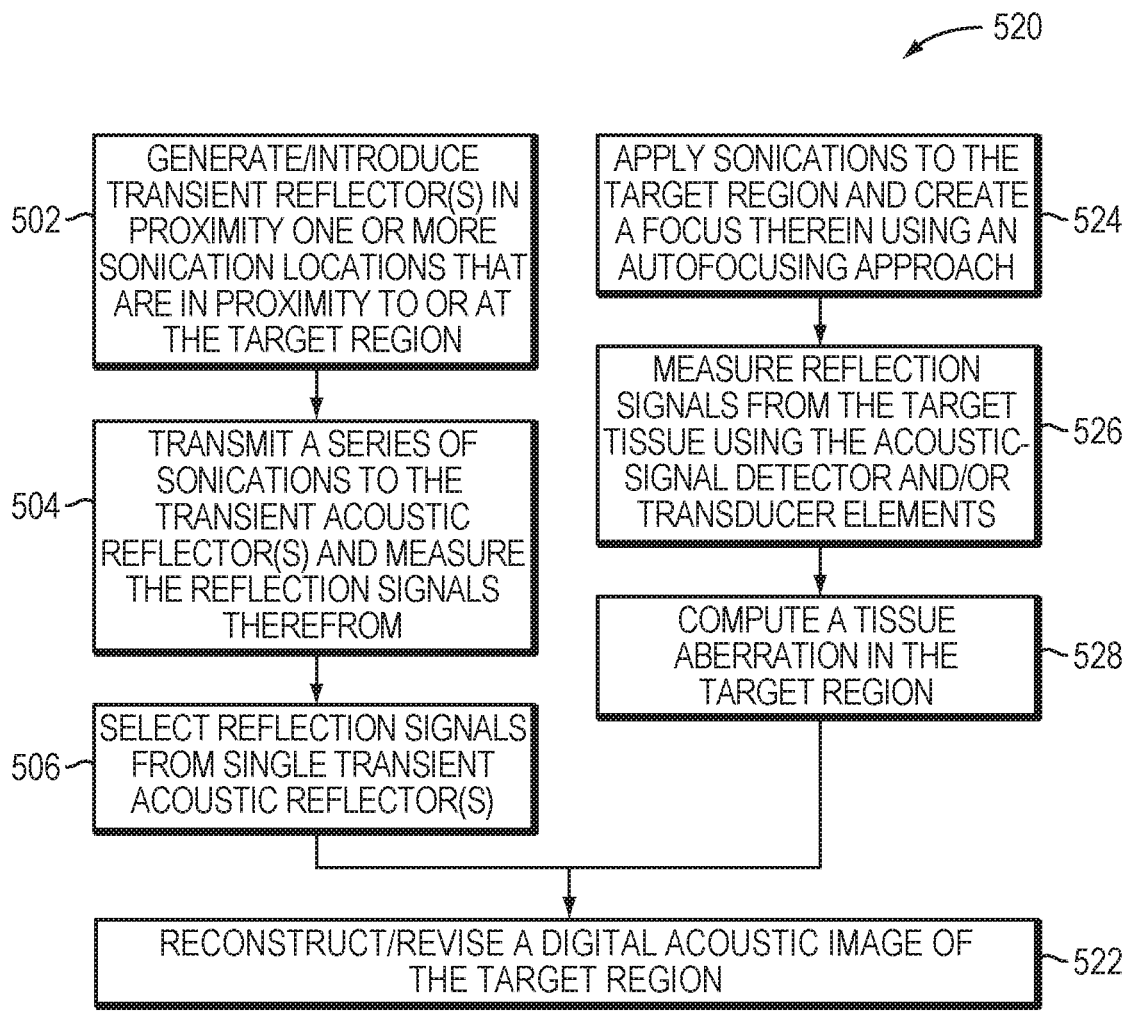
FIG. 5B is a flow chart illustrating an approach for computationally reconstructing or revising an acoustic image at the target and/or the location(s) of the acoustic reflector(s) in accordance with various embodiments.

FIG. 5B illustrates an exemplary approach 520 for computationally reconstructing/revising an acoustic image representing, for example, an acoustic field at the target and/or the location(s) of the acoustic reflector(s) in accordance herewith. Similar to approach 500, the transient acoustic reflectors (e.g., microbubbles) are first generated and/or introduced in proximity to (e.g., less than 5 mm away) one or more sonication locations that are in proximity to or at the target region (step 502). Subsequently, at least some of the transducer elements 104 are activated to transmit a series of sonications to the transient reflector(s); reflection signals therefrom can be measured using, for example, the acoustic-signal detector 124 and/or the transducer elements 104 (step 504). Optionally, the controller 108 may implement an initial signal-processing approach and/or a signal-selection approach to select reflection signals from single transient acoustic reflector(s) (step 506). Based on the selected reflection signals, the controller 108 may computationally reconstruct/revise the digital acoustic images representing, for example, acoustic fields at the target region and/or locations of the acoustic reflectors (step 522). Additionally or alternatively, the transducer may apply sonications to the target region and create a focus therein using the autofocusing approach (step 524); again, reflection signals from the target tissue may be measured using the acoustic-signal detector 124 and/or the transducer elements 104 (step 526). The controller may also compute a tissue aberration in the target region using a physical model (step 528). Based on the computed tissue aberration and the measured reflection signals from the target tissue, the controller may reconstruct/revise the acoustic image of the target region (step 522). In some embodiments, the controller 108 computationally reconstructs the acoustic images at the target region based on the computed tissue aberration and reflection signals from the target tissue and acoustic reflector(s).

Figure 5C:
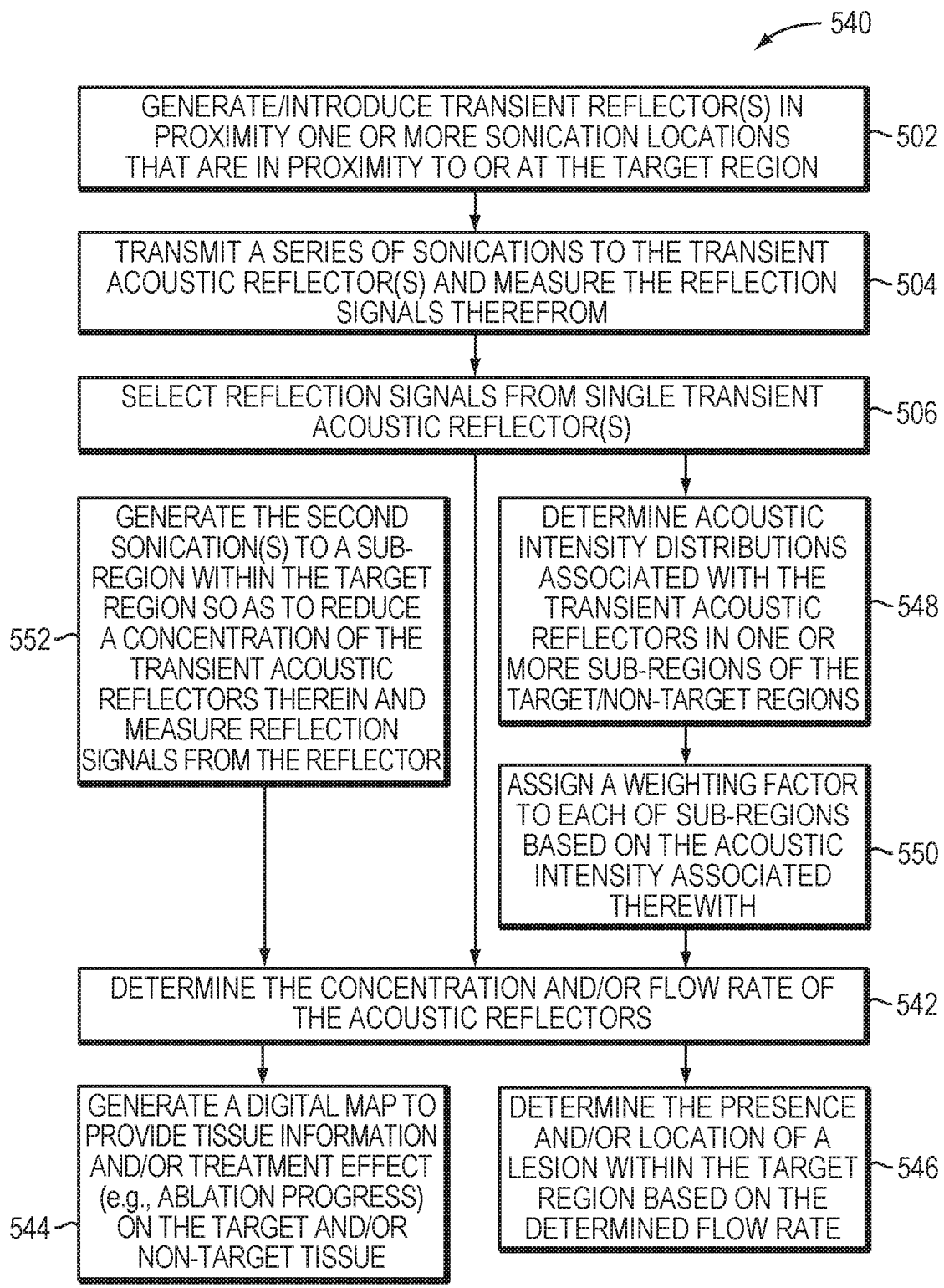
FIG. 5C is a flow chart illustrating an approach for determining tissue information of the target and/or non-target regions and/or a characteristic of the transient acoustic reflector(s) and generating a digital map providing the tissue information in accordance with various embodiments.

FIG. 5C illustrates an exemplary approach 540 for determining tissue information of the target and/or non-target regions and/or a characteristic (e.g., a concentration and/or flow rate) of the transient acoustic reflector(s) and generating a digital map providing the tissue information in accordance herewith. Similar to approaches 500, 520, the acoustic reflectors (e.g., microbubbles) are first generated and/or introduced, with an injection rate, in proximity to (e.g., less than 5 mm away) one or more sonication locations that are in proximity to or at the target region (step 502). Subsequently, at least some of the transducer elements 104 are activated to transmit a series of sonications to the transient reflector(s); reflection signals from the transient reflector(s) are then measured using, for example, the acoustic-signal detector 124 and/or the transducer elements 104 (step 504). Optionally, the controller 108 may implement an initial signal-processing approach and/or a signal-selection approach to select reflection signals from single transient acoustic reflector(s) (step 506). The controller 108 may then, based on the selected reflection signals and the injection rate of the reflectors, determine the concentration and/or flow rate of the acoustic reflectors (step 542). The determined concentration/flow rate of the acoustic reflectors may be utilized to generate a digital map providing tissue information (e.g., the mapping of blood vessels and/or the characteristic of the tissue) and/or treatment effect (e.g., ablation progress) on the target and/or non-target tissue (step 544). In addition, the controller may determine the presence and/or location of a lesion within the target region based on the determined flow rate (step 546). In some embodiments, the controller can, based on the reflection signals, determine acoustic intensity distributions associated with the transient acoustic reflectors in one or more sub-regions of the target/non-target regions (step 548). In addition, the controller may assign a weighting factor to each of sub-regions based on the acoustic intensity associated therewith (step 550). The concentration of the transient acoustic reflectors in the target/non-target regions can then be determined based on the weighted average of the acoustic intensities associated with the sub-regions (step 542). In various embodiments, the controller 108 operates the transducer to generate the second sonication(s) to a sub-region within the target region so as to reduce a concentration of the transient acoustic reflectors therein (step 552). By measuring the reflection signals from the acoustic reflectors, the controller may determine the flow rate thereof (step 542).

In general, functionality for providing information about target and/or non-target tissue and/or a characteristic of the transient acoustic reflectors and computationally reconstructing an acoustic image at the target and/or the locations of the transient acoustic reflectors, such as causing the transient reflectors to be introduced/generated in proximity one or more sonication locations that are in proximity to or at the target region, causing the transducer to transmit a series of sonications to the transient acoustic reflectors and/or target region, measuring the reflection signals from the transient acoustic reflectors and/or the target region, selecting the reflection signals, and based thereon, determining a characteristic associated with the reflectors, generating a digital map including information of the tissue located in proximity to or within the target region, determining the presence and/or location of a lesion within the target region, evaluating the treatment effect on the target region, registering the tissue information with images acquired using an imaging device (e.g., a CT device or an MRI device) different from the ultrasound transducer, computing a tissue aberration in the target region using, for example, a physical model, reconstructing an acoustic image at the target region, causing the transducer to generate the second sonication(s) to a sub-region within the target region so as to reduce a concentration of the transient acoustic reflectors therein, determining acoustic intensity distributions associated with the transient acoustic reflectors in one or more sub-regions of the target/non-target regions and assigning a weighting factor to each of sub-regions based on the acoustic intensity associated therewith, as described above, whether integrated within a controller of the imager, the administration system, and/or an ultrasound system, or provided by a separate external controller, may be structured in one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A system for computationally characterizing tissue in an anatomic target region, the system comprising:
   an ultrasound transducer comprising a plurality of transducer elements; and
   a controller configured to:
   (a) cause the transducer to generate a plurality of sonications to transient acoustic reflectors at or proximate to the target region;
   (b) measure reflection signals of the sonications off the transient acoustic reflectors;
   (c) based on the measurements, identify the reflection signals originating from single transient acoustic reflectors; and
   (d) based at least in part on the identified reflection signals, generating a digital map of tissue within the target region, the map including a tissue characteristic.

2. The system of claim 1, further comprising means for introducing a plurality of transient acoustic reflectors to the tissue within the target region.

3. The system of claim 2, wherein the means for introducing the transient acoustic reflectors comprises an administration device.

4. The system of claim 2, wherein the transient acoustic reflectors comprise microbubbles.

5. The system of claim 4, wherein the microbubbles have different characteristics, the characteristics comprising at least one of shell types, contents, half-lives in a body or sizes.

6. The system of claim 2, wherein the transient acoustic reflectors comprise targeted reflectors.

7. The system of claim 6, wherein the targeted reflectors comprise microbubbles conjugated with antibodies.

8. The system of claim 1, wherein the map further includes a mapping of blood vessels within the target region.

9. The system of claim 8, wherein the controller is further configured to register at least one of the mapping of the blood vessels or the tissue characteristic with images acquired using an imaging device different from the ultrasound transducer.

10. The system of claim 1, wherein the tissue characteristic includes at least one of a tissue type, a tissue condition, a tissue anomaly, a degree of tissue viability, a degree of vascularity, or a degree of tissue permeability.

11. The system of claim 1, wherein the controller is further configured to determine concentrations of the transient acoustic reflectors in a plurality of portions of blood vessels based at least in part on the identified reflection signals.

12. The system of claim 11, wherein the controller is further configured to determine the concentrations of the transient acoustic reflectors in a plurality of portions of the blood vessels based at least in part on an injection rate of transient acoustic reflectors.

13. The system of claim 11, wherein the controller is further configured to:
determine an acoustic intensity distribution associated with at least one of the transient acoustic reflectors in at least one of the portions of the blood vessels based at least in part on the identified reflection signals;
assign a weighting factor to each of a plurality of subregions within the at least one said blood vessel portion based on the acoustic intensity associated therewith; and
determine the concentration of the transient acoustic reflectors in the at least one said blood vessel portion based at least in part on the weighted average of the acoustic intensities associated with the sub-regions.

14. The system of claim 11, wherein the controller is further configured to determine at least one of the tissue type, tissue condition, degree of tissue permeability, or degree of tissue viability associated with at least a portion of the target region based at least in part on the corresponding concentration of the transient acoustic reflectors.

15. The system of claim 1, wherein the controller is further configured to determine a flow rate of the transient acoustic reflectors in blood vessels based at least in part on the identified reflection signals.

16. The system of claim 15, wherein the controller is further configured to map a location of a lesion within the target region based at least in part on the determined flow rate.

17. The system of claim 15, wherein the controller is further configured to:
cause the transducer to generate a second plurality of sonications to a sub-region within the target region so as to reduce a concentration of the transient acoustic reflectors therein; and
determine the flow rate based at least in part on the identified reflection signals from the transient acoustic reflectors within the sub-region.

18. The system of claim 1, wherein the controller is further configured to determine the tissue information within the target region by computing a tissue aberration for at least one transducer element using a physical model.

19. A method of computationally characterizing tissue in an anatomic target region, the method comprising:
(a) generating a plurality of sonications to transient acoustic reflectors at or proximate to the target region;
(b) measuring reflection signals of the sonications off the transient acoustic reflectors;
(c) based on the measurements, identifying the reflection signals originating from single transient acoustic reflectors; and
(d) based at least in part on the identified reflection signals, generating a digital map of tissue within the target region, the digital map including a tissue characteristic.

20. A system for computationally revising a digital acoustic image of an anatomic target region, the system comprising:
an ultrasound transducer; and
a controller configured to:
cause the transducer to generate at least one sonication focused on tissue in the anatomic target region;
measure reflection signals of the at least one sonication off the tissue;
compute a tissue aberration; and
reconstruct the digital acoustic image based at least in part on the measured reflection signals and the computed tissue aberration to thereby produce the revised digital acoustic image.

21. A method of computationally revising a digital acoustic image of an anatomic target region, the method comprising:
generating at least one sonication focused on tissue in the anatomic target region;
measuring reflection signals of the at least one sonication off the tissue;
computing a tissue aberration; and
reconstructing the digital acoustic image based at least in part on the measured reflection signals and the computed tissue aberration to thereby produce the revised digital acoustic image.

22. A system for evaluating a treatment effect on a target region, the system comprising:
an ultrasound transducer; and
a controller configured to:
(a) cause the transducer to generate a plurality of sonications to transient acoustic reflectors at or proximate to the target region in accordance with a sonication plan;
(b) measure reflection signals of the sonications off at least some of the transient acoustic reflectors; and
(c) based at least in part on the measured reflection signals, determine the treatment effect of the sonications on the target region.

23. A method of evaluating a treatment effect on a target region, the method comprising:
(a) generating a plurality of sonications to transient acoustic reflectors at or proximate to the target region in accordance with a sonication plan;
(b) measuring reflection signals of the sonications off at least some of the transient acoustic reflectors;
(c) based at least in part on the measured reflection signals, determining the treatment effect of the sonications on the target region.

* * * * *